(12) United States Patent
Colberg et al.

(10) Patent No.: US 7,026,345 B2
(45) Date of Patent: Apr. 11, 2006

(54) RESOLUTION OF 3-AMINO ALKYLNITRILES

(75) Inventors: Juan Colberg, Norwich, CT (US); Samuela Zambelli Franz, Cornedo (IT); Riccardo Motterle, Arcugnano (IT); Mariano Stivanello, Schio (IT)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/942,985

(22) Filed: Sep. 17, 2004

(65) Prior Publication Data

US 2005/0107453 A1    May 19, 2005

Related U.S. Application Data

(60) Provisional application No. 60/515,160, filed on Oct. 28, 2003.

(51) Int. Cl.
*A61K 31/4172* (2006.01)
*A61K 31/405* (2006.01)
*C07D 209/04* (2006.01)
*C07D 207/00* (2006.01)
*C07C 255/29* (2006.01)

(52) U.S. Cl. ............ 514/400; 514/419; 514/423; 548/336.1; 548/532; 548/491; 558/436; 558/440

(58) Field of Classification Search ............ 514/400, 514/419, 423; 548/336.1, 532, 491; 558/436, 558/440
See application file for complete search history.

(56) References Cited

U.S. PATENT DOCUMENTS

| 6,610,874 B1* | 8/2003 | Allen et al. ............ 558/316 |
| 2003/0065207 A1 | 4/2003 | Allen et al. ............ 558/332 |
| 2004/0002615 A1 | 1/2004 | Allen et al. ............ 558/452 |
| 2004/0087811 A1 | 5/2004 | Dreisbach et al. ......... 558/463 |
| 2005/0038281 A1* | 2/2005 | Allen et al. ............ 558/452 |

FOREIGN PATENT DOCUMENTS

JP     2004 238322     8/2004

OTHER PUBLICATIONS

Steer, D. L., et al., *The use of β-amino acids in the design of protease and peptidase inhibitors*, Letters In Peptide Science, vol. 8, pp. 241–246, (2002).
Steer, D. L., et al., *β-amino Acids: Versatile Peptidomimetics*, Current Medicinal Chemistry, vol. 9, pp. 811–822, (2002).
Marshall, R. et al., *Cobalt Ion Activation of Renal Acylase I*, J. J. Am. Chem. Soc., vol 78, pp. 4636–4642, (1956).
English translation of JP 2004-238322.

* cited by examiner

*Primary Examiner*—Johann Richter
*Assistant Examiner*—Ebenezer Sackey
(74) *Attorney, Agent, or Firm*—Gregg C. Benson; Lisa A. Samuels

(57) ABSTRACT

The present invention relates to chiral N-acetyl-alpha-amino acid salts of optically active β-amino alkylnitriles, and also to a process for preparing optically active β-amino alkylnitriles by resolving racemic β-amino alkylnitriles using chiral N-acetyl-alpha-amino acids as resolving agent.

14 Claims, No Drawings

RESOLUTION OF 3-AMINO ALKYLNITRILES

CROSS-REFERENCE TO RELATED APPLICATIONS

This application claims the benefit of U.S. Provisional application No. 60/515,160, filed Oct. 28, 2003, which is incorporated herein by reference for all purposes.

FIELD OF THE INVENTION

The present invention relates to a process for preparing optically active β-amino alkylnitriles, which are useful as building blocks in the synthesis of optically active β-amino acids and pharmaceutical drugs, via the resolution of racemic β-amino alkylnitriles using, as resolving agents, optically active N-acetyl-alpha-amino acids.

More specifically, the present invention relates to chiral N-acetyl-alpha-amino acid salts of optically active β-amino alkylnitriles and also to a process for preparing optically active β-amino alkylnitriles by resolving racemic β-amino alkylnitriles using chiral N-acetyl-alpha-amino acids as resolving agents.

BACKGROUND OF THE INVENTION

β-amino acids have been isolated in free form and show useful pharmacological properties. For example, β-amino acids can be cyclized to β-lactams, a well-known class of potential biologically active substances. These types of compounds are also excellent building blocks for the preparation of multiple natural products and have been shown to be useful tools in the synthesis of modified peptides with increased activity and in vivo stability.

Steer et al., in The Use of β-amino Acids in the Design of Protease and Peptidase Inhibitors, report that a peptidomimetic approach with significant potential has emerged in recent years that utilizes β-amino acids. The one important feature of β-amino acids is reported to be their biological stability. The biological stability is reported to be due to the fact that while β-amino acids, which have a similarity to α-amino acids in that they contain an amino terminus and a carboxyl terminus, also have two carbon atoms which separate these functional termini. As such, β-amino acids with a specific side chain can exist as the R or S isomers at either the α (C2) carbon or the β (C3) carbon resulting in a total of four possible isomers for any given side chain. This demonstrates that many more isomers are available in β-amino acids than is possible for the corresponding α-amino acids. Steer, David L.; Lew, Rebecca A.; Perlmutter, Patrick; Smith, A. Ian; Aguilar, Marie-Isabel; Letters in Peptide Science (2002), Volume Date 2001, 8(3–5), 241–246.

In β-Amino Acids: Versatile Peptidomimetics, Steer et al. review the use of β-amino acids in the design and synthesis of biologically active peptide analogues. They disclose that β-amino acids in the design of bioactive peptide analogues are rapidly expanding. The incorporation of β-amino acids is noted to be successful in creating peptidomimetics that not only have potent biological activity, but that are also resistant to proteolysis. Steer, David L.; Lew, Rebecca A.; Perlmutter, Patrick; Smith, A. Ian; Aguilar, Marie-Isabel. Current Medicinal Chemistry (2002), 9(8), 811–822.

Several methods for the preparation of enantiopure β-amino acids and their derivatives already exist. Among these methods, the conjugate addition of amines to unsaturated nitrites or esters followed by hydrolysis is useful due to raw material availability. Although this addition reaction results in high yield processes for the formation of racemic β-amino acids, most attempts to control the stereochemistry of the chiral center result in low yields and poor enantiomeric excess.

Considering the low cost of preparing racemic mixtures of β-amino alkylnitriles, resolution of these racemic substrates presents an excellent opportunity to develop a low cost process for the synthesis of optically active β-amino alkylnitriles and their corresponding β-amino acids as building blocks for making useful pharmaceutical compounds. However, little if any effort in this area appears in the scientific literature. Thus, there exists a need in the art for an efficient, low cost process for resolving racemic β-amino alkylnitriles.

SUMMARY OF THE INVENTION

According to one aspect, the present invention provides a compound of formula IIa or IIb

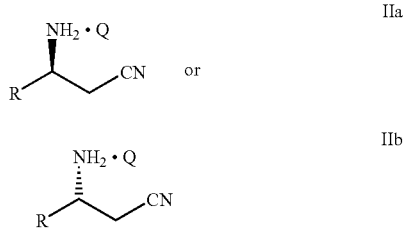

wherein R is methyl, ethyl, n-propyl, isopropyl, n-butyl, or isobutyl and Q is N-acetyl-L-alanine, N-acetyl-L-arginine, N-acetyl-L-asparagine, N-acetyl-L-aspartic acid, N-acetyl-L-cysteine, N-acetyl-L-glutamine, N-acetyl-L-glutamic acid, N-acetyl-L-histidine, N-acetyl-L-isoleucine, N-acetyl-L-leucine, N-acetyl-L-lysine, N-acetyl-L-methionine, N-acetyl-L-phenylalamine, N-acetyl-L-proline, N-acetyl-L-serine, N-acetyl-L-threonine, N-acetyl-L-tryptophan, N-acetyl-L-tyrosine, N-acetyl-L-valine, N-acetyl-D-alanine, N-acetyl-D-arginine, N-acetyl-D-asparagine, N-acetyl-D-aspartic acid, N-acetyl-D-cysteine, N-acetyl-D-glutamine, N-acetyl-D-glutamic acid, N-acetyl-D-histidine, N-acetyl-D-isoleucine, N-acetyl-D-leucine, N-acetyl-D-lysine, N-acetyl-D-methionine, N-acetyl-D-phenylalamine, N-acetyl-D-proline, N-acetyl-D-serine, N-acetyl-D-threonine, N-acetyl-D-tryptophan, N-acetyl-D-tyrosine, or N-acetyl-D-valine.

In a preferred embodiment, Q is selected from the group consisting of N-acetyl-L-alanine, N-acetyl-L-cysteine, N-acetyl-L-isoleucine, N-acetyl-L-leucine, N-acetyl-L-lysine and N-acetyl-L-valine.

In another preferred embodiment, Q is N-acetyl-L-isoleucine.

In still another preferred embodiment, Q is N-acetyl-L-valine.

According to another preferred embodiment R is ethyl.

According to another aspect of the present invention, there is provided a process for converting a racemic 3-amino-(C₃–C₇)alkylnitrile of formula I

Formula I wherein R is methyl, ethyl, n-propyl, isopropyl, n-butyl or isobutyl, to the corresponding (R) or (S) isomer of formula IIa or IIb

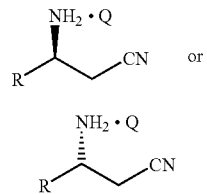

comprising combining, in a solvent, the racemic 3-amino (C$_3$–C$_7$)alkylnitrile of formula I with an N-acetyl-L-amino acid of formula Q wherein Q is N-acetyl-L-alanine, N-acetyl-L-arginine, N-acetyl-L-asparagine, N-acetyl-L-aspartic acid, N-acetyl-L-cysteine, N-acetyl-L-glutamine, N-acetyl-L-glutamic acid, N-acetyl-L-histidine, N-acetyl-L-isoleucine, N-acetyl-L-leucine, N-acetyl-L-lysine, N-acetyl-L-methionine, N-acetyl-L-phenylalamine, N-acetyl-L-proline, N-acetyl-L-serine, N-acetyl-L-threonine, N-acetyl-L-tryptophan, N-acetyl-L-tyrosine, N-acetyl-L-valine, N-acetyl-D-alanine, N-acetyl-D-arginine, N-acetyl-D-asparagine, N-acetyl-D-aspartic acid, N-acetyl-D-cysteine, N-acetyl-D-glutamine, N-acetyl-D-glutamic acid, N-acetyl-D-histidine, N-acetyl-D-isoleucine, N-acetyl-D-leucine, N-acetyl-D-lysine, N-acetyl-D-methionine, N-acetyl-D-phenylalamine, N-acetyl-D-proline, N-acetyl-D-serine, N-acetyl-D-threonine, N-acetyl-D-tryptophan, N-acetyl-D-tyrosine, or N-acetyl-D-valine in a solvent wherein the solvent is selected from the group consisting of ethanol, n-propanol, isopropanol, n-butanol, t-butanol, methanol and water or a mixture thereof.

In a preferred embodiment of the process, Q is selected from the group consisting of N-acetyl-L-alanine, N-acetyl-L-cysteine, N-acetyl-L-isoleucine, N-acetyl-L-leucine, N-acetyl-L-lysine and N-acetyl-L-valine.

In another preferred embodiment of the process, Q is N-acetyl-L-isoleucine.

In another preferred embodiment of the process, Q is N-acetyl-L-valine.

In another preferred embodiment of the process, R is ethyl.

According to another aspect of the invention, there is provided a process for converting R or S 3-amino-(C$_3$–C$_7$) alkylnitrile to racemic 3-amino-(C$_3$–C$_7$)alkylnitrile comprising combining R or S 3-aminopentanenitrile with aqueous ammonia at a temperature that is in a range of from about 30° C. to about 200° C.

According to another aspect of the invention, the racemic amino(C$_3$–C$_7$)alkylnitrile is R-3-aminopentanenitrile.

According to another aspect of the invention, there is provided a composition enriched in the compound of formula IIa or IIb as described above.

According to another aspect of the invention, there is provided a compound of formula 1

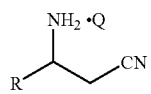

wherein R is methyl, ethyl, n-propyl, isopropyl, n-butyl, or isobutyl and Q is N-acetyl-L-alanine, N-acetyl-L-argin-ine, N-acetyl-L-asparagine, N-acetyl-L-aspartic acid, N-acetyl-L-cysteine, N-acetyl-L-glutamine, N-acetyl-L-glutamic acid, N-acetyl-L-histidine, N-acetyl-L-isoleucine, N-acetyl-L-leucine, N-acetyl-L-lysine, N-acetyl-L-methionine, N-acetyl-L-phenylalamine, N-acetyl-L-proline, N-acetyl-L-serine, N-acetyl-L-threonine, N-acetyl-L-tryptophan, N-acetyl-L-tyrosine, N-acetyl-L-valine, N-acetyl-D-alanine, N-acetyl-D-arginine, N-acetyl-D-asparagine, N-acetyl-D-aspartic acid, N-acetyl-D-cysteine, N-acetyl-D-glutamine, N-acetyl-D-glutamic acid, N-acetyl-D-histidine, N-acetyl-D-isoleucine, N-acetyl-D-leucine, N-acetyl-D-lysine, N-acetyl-D-methionine, N-acetyl-D-phenylalamine, N-acetyl-D-proline, N-acetyl-D-serine, N-acetyl-D-threonine, N-acetyl-D-tryptophan, N-acetyl-D-tyrosine, or N-acetyl-D-valine.

The term "resolving" as employed herein has its conventional meaning, i.e., converting a racemic 3-amino alkylnitrile of formula I to a product (i.e. a composition)enriched in the corresponding (R) or (S) isomer. An enriched composition is one that contains a higher abundance or proportion of one stereoisomer over the other. Thus, an enriched composition generally contains a higher proportion of a desired stereoisomer (i.e. an enantiomer) relative to the racemate.

In the formulas herein, and unless otherwise indicated, the amino-carbon bonds have their art-recognized stereochemical meanings. For example, in formula I above the straight-line amino-carbon bond represents the racemate. A thickened amino-carbon bond, as in formula IIa (see below), is above the plane of the page. A dashed or dotted amino-carbon bond, as in formula IIb, is below the plane of the page.

Those skilled in the art will readily appreciate that the symbol · in formulas I, IIa and IIb denotes a salt pair.

The salt formed between the optically active N-acetyl-alpha amino acid, Q, and either the (R)-stereoisomer or the (S)-stereoisomer of the β-amino alkylnitrile substrate has the formula IIa or IIb

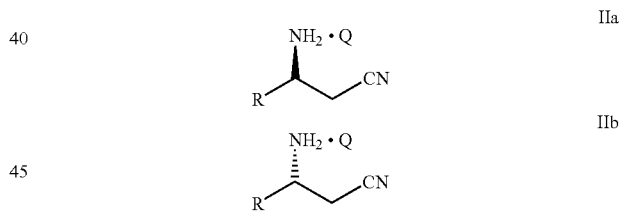

wherein Q, R, and the amino-carbon bonds each have the meaning given above. The particular salt formed depends, of course, on the stereochemistry of the particular N-acetyl-alpha amino acid used to resolve the β-amino alkylnitrile. If the desired stereoisomer is contained in the salt, the salt generally precipitates and can be isolated, for example by filtration. Q can then be displaced to yield the desired optically active β-amino alkylnitrile. If, on the other hand, the desired isomer is contained in the mother liquor, the mother liquor can be concentrated to yield the desired optically active β-amino alkylnitrile.

The inventors determined that optically active N-acetyl-alpha-amino acids, defined herein as Q, may be used to resolve racemic β-amino alkylnitriles of the formula I. The racemic β-amino alkylnitrile is reacted with (also referred to herein as "treated") an N-acetyl alpha-amino acid stereoisomer to form either of the corresponding optically active salts of formula IIa and IIb, in excellent enantiomeric purity and overall yield. In general, the salt of formula IIa or IIb that is formed precipitates, leaving the remaining β-amino alkylnitrile stereoisomer dissolved in the mother liquor. If the desired stereoisomer is contained in the salt, the salt can be isolated, for example by filtration, and Q can be displaced to yield the desired optically active β-amino alkylnitrile. If, on the other hand, the desired isomer is contained in the mother liquor, the mother liquor can be concentrated to yield the desired optically active β-amino alkylnitrile. Optionally, the mother liquor can first be extracted with a suitable (immiscible) extracting solvent, for example a solvent having a low boiling point, and then concentrated by evaporating off the low boiling solvent.

A specific exemplary embodiment of this invention relates to a process as described above, wherein L-N-acetylvaline is used as the resolving agent and an alcohol, for example ethanol, is employed as the solvent for the crystallization of the β-amino alkylnitrile-L-N-acetylvalinate salt. In another specific embodiment, the inventors determined that the above procedure may be used to prepare (R)-3-aminopentanitrile from the racemic mixture, using N-acetylamino acids. More specifically, L-N-acetylvaline is used as a resolving agent followed by free-basing the valinate salt using known art procedures.

DETAILED DESCRIPTION OF THE INVENTION

It has been discovered that the resolution of a racemic 3-amino alkylnitrile by treatment with L-N-acetyl amino acids can provide a high yielding resolution reaction with very high selectivity. In addition, it has been discovered that this approach provides a low cost/high efficiency procedure for synthesizing a compound of interest such as R-3-aminopentanenitrile. Certain processes for the manufacture of optically active β-amino alkylnitriles are provided as further features of the invention and are described below and in the experimental section.

All starting materials are commercially available; moreover, their syntheses will be readily apparent to a skilled individual. See, for example Synthesis of N-acetyl Amino acids, Marshall, J.J. AM. Chem. Soc. 1956, 78, 4636.

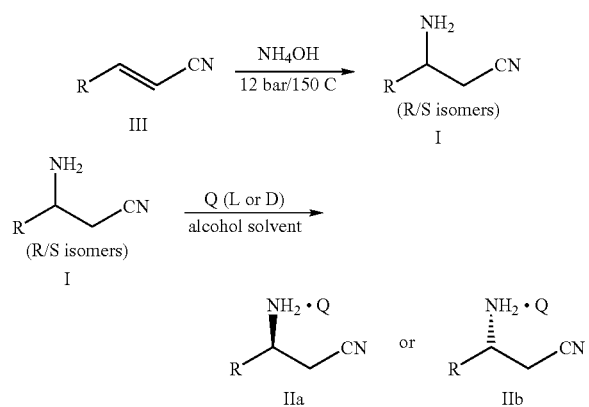

In the above, R and Q are as previously defined.

Scheme 1, as depicted above, provides the preparation of the chiral (R) or (S) 3-amino alkylnitrile N-acetyl-alpha-aminoacid salt of formula IIa or IIb starting from an appropriate alkyl-2-enenitrile of formula III. The alkyl-2-ene nitrile of formula III is reacted with aqueous ammonium hydroxide, preferably at a pressure of approximately 12 bar and a temperature of approximately 150° C. to provide the racemic 3-amino alkyl of formula I. The chiral 3-amino alkylnitrile N-acetyl-alpha-amino acid salt of formula IIa or IIb is then prepared by reacting the racemic 3-amino alkylnitrile of formula I with an appropriate chiral N-acetyl-alpha-amino acid Q preferably, in an alcoholic or aqueous/alcoholic solvent, at a temperature of about −20° to about 120° C.

The salt formation is most preferably conducted using ethanol/water as the solvent mixture and in a range of about 0.5 to about 1.1 moles of formula Q per mole of β-amino alkylnitrile of formula I. The reaction may be carried out at temperatures ranging from about room temperature to about 80° C. The reaction is preferably carried out at a temperature ranging from about 65° C. to about 80° C. The reaction is continued until a solution is obtained. The mixture is then cooled, filtered and the desired isomer is isolated, for example by filtration if it separates from the mother liquor as the salt, or by evaporation if it remains in the mother liquor as the unprecipitated remaining β-amino alkylnitrile stereoisomer.

A preferred method for preparing the chiral 3-amino alkylnitrile N-acetyl-alpha-amino acid salt of formula IIa or IIb employs reacting 0.9 equivalents of an appropriate chiral N-acetyl-alpha-amino acid of formula Q with 1.0 equivalents of the racemic 3-amino alkylnitrile in aqueous ethanol. More particularly, the racemic 3-amino alkylnitrile of formula I is added to the chiral N-acetyl-alpha-amino acid Q in aqueous ethanol at approximately 65° to 70° C. The reaction mixture is then heated at reflux until a homogenous solution is obtained. The reaction mixture is then cooled to approximately 60° C. and maintained at this temperature for a minimum of 30 minutes. The reaction mixture is then further cooled to 0° C. and the chiral 3-amino-alkylnitrile-N-acetyl-alpha-aminoacid salt of formula I, which has precipitated, is separated and collected by filtration. The filtrate will be enriched in the remaining steroisomer. If the filtrate is enriched in the undesired isomer, it can be treated as described above to racemize the steroisomer and then recycled through the resolution procedure. If it contains the desired stereoisomer, it can be concentrated as by evaporation to recover the isomer, optionally with an intermediate extraction step.

Those skilled in the art will readily appreciate that this procedure is generally applicable to any of the β-amino alkylnitriles useful in this invention, realizing that adjustments to the solvent (or solvent system if a mixture is used), temperature and particular chiral N-acetyl amino acid may be required to optimize yield.

As previously noted, to maximize atom utilization the invention provides a process to racemize the undesired isomer as shown in Scheme 2. The chiral 3-amino($C_3$–$C_7$) alkylnitrile is reacted with aqueous ammonium hydroxide at about 12 bar at approximately 120° C. to 150° C. for a period of 2 to 24 hours. The reaction mixture is then concentrated in vacuo and the resulting crude racemic 3-amino($C_3$–$C_7$) alkylnitrile can be further isolated by vacuum distillation.

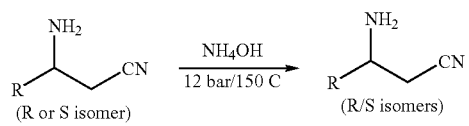

The resulting racemic mixture can then be resolved according to known procedures disclosed herein, that is, the racemic mixture can be reacted with an N-acetylamino acid defined herein as Q to produce the enantiomerically enriched salt of formula IIa or IIb in accordance with the conditions described above in Scheme 1.

EXAMPLES

Example I

Synthesis of N-acetyl-L-valine

L-Valine (200 g, 1.7 mol eq) is dissolved in water (500 mL) followed by the addition of NaOH (30%, 170 mL). The mixture is cooled to 0°–5° C. followed by the addition of acetic anhydride (32 ml, 1.4 eq.). Sodium hydroxide (30%, 34 mL) is added while keeping the temperature at 0°–5° C. Acetic anhydride and 30% NaOH alternate additions are repeated six time while keeping the temperature (acetic anhydride, 6×32 mL; 30% NaOH 6×34 mL). After all the additions are completed, the mixture is stirred for an additional two hours at 0° C. Hydrochloric acid (32%, 380 mL) is added to lower the pH below 3 while keeping the temperature at 0° C. The resulting slurry is granulated for 12 hours, filter and the cake washed with HCl (0.1 N, 100 mL). The wet N-acetyl-L-valine was dried to produce 233 g (86% yield).

Example II

Resolution of 3-aminopentanenitrile with N-acetyl-L-valine

N-acetyl-L-valine (145.4 g, 0.91 mol eq) is combined with ethanol (1425 mL) and water (75 mL) in a vessel equipped with agitation and condenser. The mixture is heated to 65°–70° C. followed by the addition (with a syringe) of racemic 3-aminopentanenitrile. The mixture is heated at reflux until a complete solution is obtained. The mixture is cooled to 60° C. and held at this temperature for a minimum of 30 minutes. The mixture is cooled to 0° C. and the salt is isolated by filtration.

Example III

Resolution of 3-aminopentanenitrile with N-acetyl-L-isoleucine

N-acetyl-L-isoleucine (157 g, 0.91 mol eq) is combined with ethanol (250 mL) and water (75 mL) in a vessel equipped with agitation and condenser. The mixture is heated to 65°–70° C. followed by the addition of racemic 3-aminopentanenitrile. The mixture is heated at reflux until a complete solution is obtained. The mixture is cooled to 60° C. and held at this temperature for a minimum of 30 minutes. The mixture is cooled to 0° C. and the salt isolated by filtration (70% yield based in a maximum of 50% and 99.8% ee).

Example IV

Racemization of R-3-aminopentanenitrile

R-3-aminopentanenitrile (197 g, 2.1 mol eq) is combined with ammonia 30% water solution (930 mL, 14.7 mol eq.) in a suitable pressure rated vessel and the mixture is heated to 130° C. After 6 hours the mixture is cooled and analyzed for complete racemization. The mixture is concentrated under vacuum (15 mmHg, 88 C) to 300 mL. The crude product is distilled under vacuum for further purification to obtain 160 g of the racemic mixture (77% yield, 95% GC pure, 50/50% R/S).

Example V

Free Basing of 3-aminopentanenitrile N-acetyl-L-valine Salt 3-aminopentanenitrile N-acetyl-L-valine salt (230 g) is combined with dichloromethane (713 mL). To the mixture is added a sodium hydroxide aqueous solution (98 mL, 30% w/w) and the mixture stirred at 20°–25° C. for 1 hour. The lower organic phase is separated and the upper aqueous phase washed with additional dichloromethane (2×180 mL). The organic layers are combined, concentrated and the optically active 3-aminopentanenitrile isolated by distillation (80% yield, 99.8% ee)

Example VI

Preparation of 3-Amino-pentanenitrile L-Acetyl-L-valine Salt

A 3 l flask equipped with mechanical stirrer, thermometer, dropping funnel, oil bath, was charged with N-acetyl-L-valine (145.4 g), denaturated ethanol (denatured with about 5% methanol and 3% cyclohexane) (1425 ml) and water (75 ml). The mixture was heated under stirring to 65–70° C. and 150 g of 3-aminopentanenitrile were added. The solution was heated to reflux (about 75° C.) until obtaining a complete clear solution that was then slowly cooled to 65° C. Always under stirring the mixture was seeded with some diasteromerically pure 3-amino-pentanenitrile-L-acetyl-L-valine salt and stirred at 60° C. for 1 hour. The thick suspension was then cooled to 0° C. over a period of 3 hours and stirred at 0° C. for 2 hours. The obtained salt was filtered and washed with 2×75 ml of ethanol. The optical purity of the wet product was 89.8% (A %). The wet salt was charged in a 2 l flask with standard equipment and 900 ml of denaturated ethanol were added. The suspension was heated to reflux, stirred for 1 hour at reflux temperature and then cooled to RT over a period of 2 hours. After 2 more hours of stirring at RT, the obtained salt was filtered and washed with 2×150 ml of denaturated ethanol. The product was dried at 40° C. obtaining 118.3 g of 3-aminopentanenitrile-L-acetyl-L-valine salt, white crystalline solid (optical purity: 99.8% R; yield: 60% of theoretical).

Example VII

Preparation of 3-Amino-pentanenitrile L-Acetyl-L-valine Salt

A 3 l flask equipped with mechanical stirrer, thermometer, dropping funnel, oil bath, was charged with N-acetyl-L-valine (200.0 g) denaturated ethanol (denatured with about 5% methanol and 3% cyclohexane) (2000 ml) and water (100 ml). The mixture was heated under stirring to 65–70° C. and 3-aminopentanenitrile (206.4 g) was added within 30 min. The solution was heated to reflux (about 75° C.) until obtaining a complete clear solution which was then slowly cooled to 65° C. Always under stirring the mixture was seeded with some diasteromerically pure 3-amino-pentanenitrile-L-acetyl-L-valine salt and stirred at 60° C. for 1 hour. The thick suspension was then slowly cooled to 20° C. over a period of 3 hours and stirred at 20° C. for 18 hours (overnight). The suspension was hence cooled to 5° C. and stirred 3 hours. The precipitate salt was filtered and washed with denaturated ethanol (3× 100 ml) and dried in an vacuum try-drier at 40° C./10 mbar until constant weight, obtaining 3-amino-pentanenitrile-L-acetyl-L-valine salt (228.7 g), white crystalline solid (yield 84.8%) having optical purity 97.7%.

Example VIII

Preparation of 3-Amino-pentanenitrile L-acetyl-L-isoleucine Salt

A 250 ml flask equipped with mechanical stirrer, thermometer, dropping funnel, oil bath, was charged with 3-aminopentanenitrile (5 g), N-acetyl-L-isoleucine (8.8 g), and of denaturated ethanol (denatured with about 5% methanol and 3% cyclohexane) (97 ml). The solution was heated to reflux until obtaining a complete clear solution which was then slowly cooled to 68° C. Always under stirring the mixture was seeded with some diasteromerically enriched 3-amino-pentanenitrile-L-acetyl-L-isoleucine salt and stirred at 65–70° C. for 2 hour. The thick suspension was then cooled slowly to RT. The obtained salt was filtered and washed with ethanol. The product was dried at 50° C. obtaining 3-amino-pentanenitrile-L-Acetyl-L-isoleucine salt (7.3 g), white crystalline solid (optical purity: 76% R; yield: 112% of theoretical).

The obtained salt was charged in a 250 ml flask with standard equipment and methyl ethyl ketone (73 ml) was added. The suspension was heated to reflux, stirred for 1 hour at reflux temperature and then slowly cooled to 60° C. The obtained salt was filtered and washed with methyl ethyl ketone. The product was dried at 50° C. obtaining 3-amino-pentanenitrile-L-Acetylisoleucine salt (5.2 g), white crystalline solid (optical purity: 98.2% R; yield: 71.9% of theoretical).

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of formula IIa or IIb

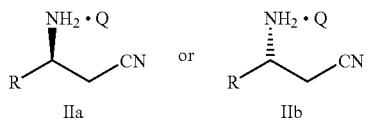

wherein R is methyl, ethyl, n-propyl, isopropyl, n-butyl, or isobutyl and Q is N-acetyl-L-alanine, N-acetyl-L-arginine, N-acetyl-L-asparagine, N-acetyl-L-aspartic acid, N-acetyl-L-cysteine, N-acetyl-L-glutamine, N-acetyl-L-glutamic acid, N-acetyl-L-histidine, N-acetyl-L-isoleucine, N-acetyl-L-leucine, N-acetyl-L-lysine, N-acetyl-L-methionine, N-acetyl-L-phenylalamine, N-acetyl-L-proline, N-acetyl-L-serine, N-acetyl-L-threonine, N-acetyl-L-tryptophan, N-acetyl-L-tyrosine, N-acetyl-L-valine, N-acetyl-D-alanine, N-acetyl-D-arginine, N-acetyl-D-asparagine, N-acetyl-D-aspartic acid, N-acetyl-D-cysteine, N-acetyl-D-glutamine, N-acetyl-D-glutamic acid, N-acetyl-D-histidine, N-acetyl-D-isoleucine, N-acetyl-D-leucine, N-acetyl-D-lysine, N-acetyl-D-methionine, N-acetyl-D-phenylalamine, N-acetyl-D-proline, N-acetyl-D-serine, N-acetyl-D-threonine, N-acetyl-D-tryptophan, N-acetyl-D-tyrosine, or N-acetyl-D-valine.

2. The compound according to claim 1 wherein Q is selected from the group consisting of N-acetyl-L-alanine, N-acetyl-L-cysteine, N-acetyl-L-isoleucine, N-acetyl-L-leucine, N-acetyl-L-lysine and N-acetyl-L-valine.

3. The compound according to claim 2 wherein Q is N-acetyl-L-isoleucine.

4. The compound according to claim 2 wherein Q is N-acetyl-L-valine.

5. The compound according to any of claims 1–4 wherein R is ethyl.

6. A process for converting a racemic 3-amino-($C_3$–$C_7$) alkylnitrile of formula I

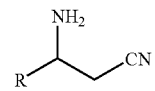

wherein R is methyl, ethyl, n-propyl, isopropyl, n-butyl or isobutyl, to the corresponding (R) or (S) isomer of formula IIa or IIb

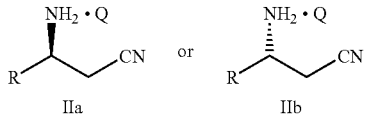

comprising combining, in a solvent, the racemic 3-amino ($C_3$–$C_7$)alkylnitrile of formula I with an N-acetyl-L-amino acid of formula Q wherein Q is N-acetyl-L-alanine, N-acetyl-L-arginine, N-acetyl-L-asparagine, N-acetyl-L-aspartic acid, N-acetyl-L-cysteine, N-acetyl-L-glutamine, N-acetyl-L-glutamic acid, N-acetyl-L-histidine, N-acetyl-L-isoleucine, N-acetyl-L-leucine, N-acetyl-L-lysine, N-acetyl-L-methionine, N-acetyl-L-phenylalamine, N-acetyl-L-proline, N-acetyl-L-serine, N-acetyl-L-threonine, N-acetyl-L-tryptophan, N-acetyl-L-tyrosine, N-acetyl-L-valine, N-acetyl-D-alanine, N-acetyl-D-arginine, N-acetyl-D-asparagine, N-acetyl-D-aspartic acid, N-acetyl-D-cysteine, N-acetyl-D-glutamine, N-acetyl-D-glutamic acid, N-acetyl-D-histidine, N-acetyl-D-isoleucine, N-acetyl-D-leucine, N-acetyl-D-lysine, N-acetyl-D-methionine, N-acetyl-D-phenylalamine, N-acetyl-D-proline, N-acetyl-D-serine, N-acetyl-D-threonine, N-acetyl-D-tryptophan, N-acetyl-D-tyrosine, or N-acetyl-D-valine, wherein the solvent is selected from the group consisting of ethanol, n-propanol, isopropanol, n-butanol, t-butanol, methanol and water or a mixture thereof.

7. The process according to claim 6 wherein Q is selected from the group consisting of N-acetyl-L-alanine, N-acetyl-L-cysteine, N-acetyl-L-isoleucine, N-acetyl-L-leucine, N-acetyl-L-lysine and N-acetyl-L-valine.

8. The process according to claim 7 wherein Q is N-acetyl-L-isoleucine.

9. The process according to claim 7 wherein Q is N-acetyl-L-valine.

10. The process according to any of claims 6–9 wherein R is ethyl.

11. A process for converting R or S 3-amino-($C_3$–$C_7$)alkylnitrile to racemic 3-amino-($C_3$–$C_7$)alkylnitrile comprising combining R or S 3-aminopentanenitrile with aqueous ammonia at a temperature that is in a range of from about 30° C. to about 200° C.

12. The process according to claim 11 wherein the racemic amino($C_3$–$C_7$)alkylnitrile is R-3-aminopentanenitrile.

13. A composition enriched in a compound according to any of claims 1 through 4.

14. A compound of formula I

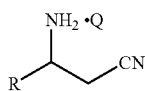

wherein

R is methyl, ethyl, n-propyl, isopropyl, n-butyl, or isobutyl and Q is N-acetyl-L-alanine, N-acetyl-L-arginine, N-acetyl-L-asparagine, N-acetyl-L-aspartic acid, N-acetyl-L-cysteine, N-acetyl-L-glutamine, N-acetyl-L-glutamic acid, N-acetyl-L-histidine, N-acetyl-L-isoleucine, N-acetyl-L-leucine, N-acetyl-L-lysine, N-acetyl-L-methionine, N-acetyl-L-phenylalamine, N-acetyl-L-proline, N-acetyl-L-serine, N-acetyl-L-threonine, N-acetyl-L-tryptophan, N-acetyl-L-tyrosine, N-acetyl-L-valine, N-acetyl-D-alanine, N-acetyl-D-arginine, N-acetyl-D-asparagine, N-acetyl-D-aspartic acid, N-acetyl-D-cysteine, N-acetyl-D-glutamine, N-acetyl-D-glutamic acid, N-acetyl-D-histidine, N-acetyl-D-isoleucine, N-acetyl-D-leucine, N-acetyl-D-lysine, N-acetyl-D-methionine, N-acetyl-D-phenylalamine, N-acetyl-D-proline, N-acetyl-D-serine, N-acetyl-D-threonine, N-acetyl-D-tryptophan, N-acetyl-D-tyrosine, or N-acetyl-D-valine.

* * * * *